United States Patent
Drasler (10) Patent No.: US 10,595,842 B2
(45) Date of Patent: Mar. 24, 2020

(54) EXPANDABLE CARDIAC ACCESS CATHETER

(71) Applicant: William Joseph Drasler, Minnetonka, MN (US)

(72) Inventor: William Joseph Drasler, Minnetonka, MN (US)

(*) Notice: Subject to any disclaimer, the term of this patent is extended or adjusted under 35 U.S.C. 154(b) by 399 days.

(21) Appl. No.: 15/460,347

(22) Filed: Mar. 16, 2017

(65) Prior Publication Data

US 2018/0263658 A1  Sep. 20, 2018

(51) Int. Cl.
| | | |
|---|---|---|
| *A61B 17/34* | (2006.01) | |
| *A61B 17/02* | (2006.01) | |
| *A61F 2/24* | (2006.01) | |
| *A61B 17/00* | (2006.01) | |
| *A61B 17/12* | (2006.01) | |

(52) U.S. Cl.
CPC ...... *A61B 17/0218* (2013.01); *A61B 17/3478* (2013.01); *A61F 2/2466* (2013.01); *A61B 2017/00243* (2013.01); *A61B 2017/00247* (2013.01); *A61B 2017/1205* (2013.01); *A61B 2017/3488* (2013.01); *A61F 2/2427* (2013.01)

(58) Field of Classification Search
CPC ............ A61B 17/0218; A61B 17/3478; A61B 2017/3486; A61F 2/2466; A61M 25/0084; A61M 25/10; A61M 25/0067
See application file for complete search history.

(56) References Cited

U.S. PATENT DOCUMENTS

| | | | | |
|---|---|---|---|---|
| 5,006,119 | A  * | 4/1991  | Acker    | A61B 18/08 604/96.01 |
| 6,059,752 | A  * | 5/2000  | Segal    | A61F 2/958 604/104 |
| 6,325,815 | B1 * | 12/2001 | Kusleika | A61B 17/221 606/200 |
| 6,599,267 | B1 * | 7/2003  | Ray      | A61M 25/0074 604/102.01 |
| 8,975,233 | B2 * | 3/2015  | Stein    | A61K 31/55 514/25 |
| 2006/0271093 | A1 * | 11/2006 | Holman | A61F 2/958 606/194 |
| 2009/0259288 | A1 * | 10/2009 | Wijay | A61F 2/954 623/1.11 |
| 2009/0292241 | A1 * | 11/2009 | von Oepen | A61F 2/958 604/96.01 |
| 2016/0045219 | A1 * | 2/2016 | Guala | A61M 25/0194 606/185 |
| 2016/0058489 | A1 * | 3/2016 | Fischell | A61B 18/00 |

* cited by examiner

*Primary Examiner* — Matthew F Desanto (57) ABSTRACT

An access catheter provides access for a large bore stiff therapeutic catheter across the atrial septum from above via the superior vena cava. The access catheter has an expandable member that direct a delivery tube outwards in a radial direction to place a delivery tube opening into direct contact with the fossa ovalis. The braided expandable member allows blood flow to pass when it is expanded; the expandable member provides support against the opposite wall of the right atrium. A hollow dilator tube enters the delivery tube to form a tenting shape to the fossa and a guidewire is passed across the fossa ovalis. Standard procedure allows delivery of the therapeutic catheter over the guidewire.

11 Claims, 11 Drawing Sheets

EXPANDABLE CARDIAC ACCESS CATHETER

CROSS REFERENCE TO RELATED APPLICATIONS

This patent application makes reference to and thereby incorporates all information found in the provisional patent application No. 62/391,441 entitled Cardiac Atrial Septal Access Catheter filed 29 Apr. 2016 by William J. Drasler.

BACKGROUND

Percutaneous delivery of medical devices across a septum of the vasculature or across a septum of the heart can be challenging for the physician. For example, delivery of a catheter across the atrial septum from the right atrium to the left atrium for delivery of an atrial ablation catheter, atrial appendage occlusion catheter, mitral valve therapeutic devices, and transcatheter mitral valve replacement (TMVR) devices requires an accurate puncture across the atrial septum to ensure patient safety and to provide an efficient alignment for the therapeutic catheter towards its intended target.

Often the transseptal puncture is made from an access site of the femoral vein and with the catheter traveling from below the heart through the inferior vena cava. The current catheters and devices used for crossing the septum from below include the Mullins sheath and the Brockenbrough needle and catheter. Access from below takes advantage of the native structures of the atrial septum to help guide the placement of such catheters into the correct location for transseptal puncture. For example, the thickened limbus tissue located on the superior aspect of the fossa ovalis serves to provide a stabilizing shelf and a locating member that provides the physician with an opportunity for a safe puncture across the fossa ovalis of the atrial septum. Such punctures that are accessed from the inferior vena cava end of the right atrium work adequately for smaller profile catheters ranging from 8-14 French that are reasonably flexible such as atrial ablation catheters, for example.

Delivery of larger diameter (20-26 French) and stiff TMVR devices across the atrial septum from below via the inferior vena cava are forced to undergo a large curve within the left atrium (LA) prior to extending across the mitral annulus. The alignment of such stiff and high profile catheters with the axis of the mitral annulus cannot be easily accomplished from below. Access across the atrial septum from above via the superior vena cava would allow an improved alignment of a large profile stiff catheter across the mitral annulus. The current catheters and tools used to cross the atrial septum from below do not provide a safe and efficient access across the fossa ovalis from above. The limbus which provided a stabilizing ledge for the catheters from below do not provide any such stabilizing benefit from a superior access via the superior vena cava. What is needed is a device that can reliably provide access across the fossa ovalis for the high profile devices (such as a TMVR device) transseptally in a safe, easy, and reliable manner with good support from the surrounding tissues and good alignment with the axis of the mitral annulus.

SUMMARY

An access catheter is described that provides efficient access across the atrial septum for a large profile stiff catheter and alignment with the axis of the mitral annulus. The access catheter can be used to provide access across the atrial septum from above via the SVC which allows the alignment of a TMVR catheter with the mitral valve axis to be in greater alignment than can be achieved via the atrial septal access from below via the IVC. The difficulty of puncturing the fossa ovalis near the limbus which is difficult via access from above using standard catheters is improved using the device of the present invention. Alternately, the access catheter of the present invention can also be used to deliver a high profile device from below via the IVC.

In one embodiment the access catheter of the present invention has two movable coaxial tubes or shafts that are positioned one within the other. The outer shaft is attached to a proximal end of a braided tube and the inner shaft is attached to a distal end of the braided tube. When the inner tube is placed into tension the braided tube assumes a large diameter expanded configuration with a large diameter perimeter located midway between each end of the braided tube. Located on the outside of the inner shaft and within the inner lumen of the braided tube is the distal portion of a delivery tube that is bonded to the large diameter perimeter of the braided tube; the distal portion of the delivery tube is directed radially outwards so that it can deliver a puncturing needle or other sharp or pointed member across the atrial septum through a distal opening in the delivery tube that is positioned adjacent to the atrial septum. The opposite side of the large diameter perimeter (i.e., 180 degrees around the perimeter of the expanded structure) is resting against the opposite wall of the right atrium (i.e., the lateral wall located 180 degrees away from the atrial septum). This opposite side of the perimeter of the braided tube provides support to allow a puncture device such as a beveled needle to push through the atrial septum. The opening in the delivery tube can be positioned anywhere desired on the atrial septum including at locations that are just below or inferior to the limbus, in a posterior aspect of the fossa ovalis, or in a location outside of the fossa ovalis. Locating the puncture site appropriately on the atrial septum allows the trajectory of the subsequently placed TMVR device or other large profile catheter to remain in alignment with the axis of the mitral annulus.

The distal portion of the delivery tube extends from its location within the braided tube to a position adjacent to or along-side of the shaft of the catheter to the proximal end of the catheter. The delivery tube will carry a crossing catheter (such as a beveled needle, for example) that is intended to cross the atrial septum from the right atrium (RA) to the left atrium (LA). The portion of the delivery tube that is located within the braided tube has a gentle curve that is able to redirect a crossing catheter such as a beveled needle from an axial direction that is aligned with the central shaft to a radial direction perpendicular to the catheter shaft and across the atrial septum with a full radial component. It is noted that if a small radial dimension such as the diameter of the catheter shaft were to direct an opening to the side or perpendicular to the catheter linear axis through the wall of the catheter shaft, that such an opening would not be able to redirect a crossing catheter or other catheter member or wire passing axially through such a catheter to extend out of such opening into a full radial direction as required by the present invention. A much larger dimension such as the radius of the expandable member is required to redirect a crossing catheter to a direction with full radial componency perpendicular to the linear axis of the catheter shaft.

A small-length (i.e., the dimension of a catheter shaft diameter) radially directed channel of a standard catheter shaft used to cross the atrial septum, for example, cannot redirect a crossing catheter that is travelling axially along a catheter shaft to have a full radial direction, and hence cannot provide crossing of the atrial septum in precisely an optimal location and full radial direction as can be accomplished with the present invention.

A dilator tube can be placed within the delivery tube of the present invention. The dilator tube allows a tent-like shape to be formed within the fossa ovalis of the atrial septum for identifying the proper location of the puncture. The dilator tube also allows passage of a crossing catheter within the lumen of the dilator tube; such crossing catheters can include beveled needles, blunt needles, sharp pins or mandrels, and guidewires.

Other embodiments are presented for the expandable structure other than a braided tube. These embodiments function in a manner that is similar to the braided tube. The embodiments of the present invention are actively described to have application to crossing the atrial septum from above via the SVC, but it is understood that the invention can be equally applied to provide access across the wall of an atrial septum, for example, as well as crossing the wall structure of any tubular member of the body including vascular and nonvascular tubular members of the body. The dimensions provided in this application are understood to require proportional modification for tubular members that are smaller or larger than those presented herein.

DETAILED DESCRIPTION

Figure 1A:
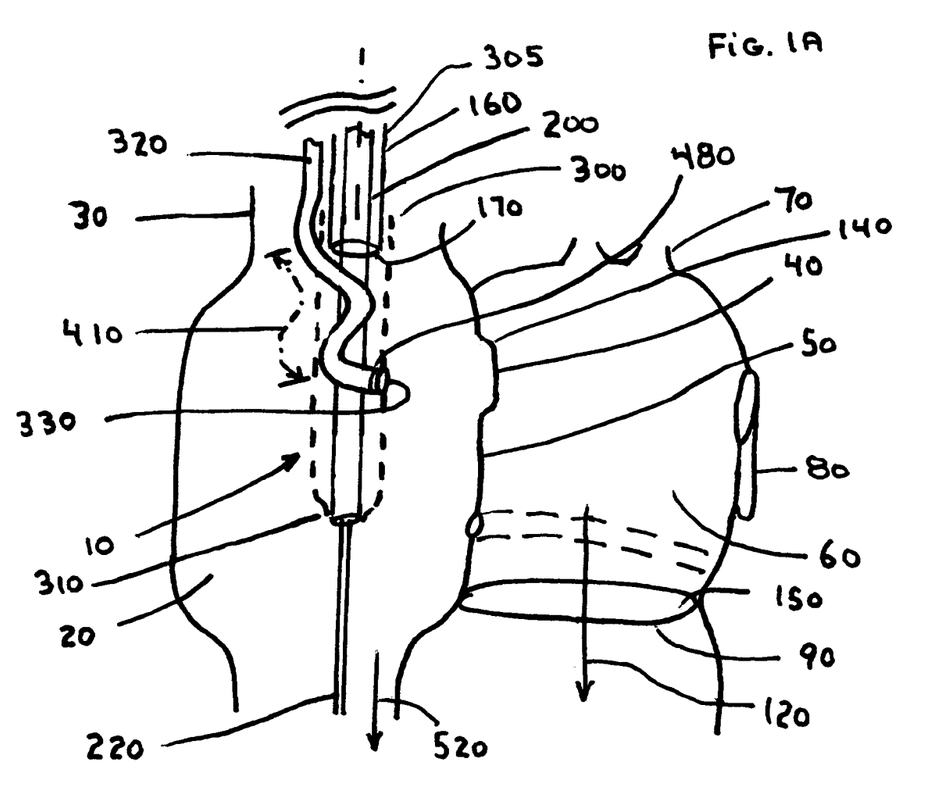
FIG. 1A is a perspective view of an unexpanded access catheter positioned within the right atrium of the heart showing the delivery tube with a serpentine shape.

One embodiment of the access catheter (10) of the present invention is shown in FIG. 1A in a non-expanded configuration. The access catheter (10) is delivered via the jugular vein, the subclavian vein, femoral vein or other large vein, blood vessel, or tubular member of the body. In this example the access catheter (10) is entering the right atrium, (RA) (20) from the superior vena cava (SVC) (30) and will be providing access for an ancillary device such as a sheath, dilator, needle, sharp needle, guidewire (220) or catheter to cross the fossa ovalis (40) or other location within the atrial septum (50). Once across the atrial septum (50), a therapeutic device or catheter can be delivered into the left atrium (LA) (60) for a variety of purposes including ablation of atrial tissue or tissues surrounding the pulmonary veins (70), occluding the left atrial appendage (80), treating mitral valve dysfunction, or delivery of a transcatheter mitral valve replacement (TMVR) device across the mitral annulus (90). For delivery of a stiff and high profile (i.e., 20-30 French) TMVR device, for example, transseptal access across the atrial septum (50) from the SVC (30) allows an improved angle of delivery across the mitral annulus (90) that allows better alignment and collinearity of the axially-directed axis (100) of the TMVR catheter (110) delivered over a guidewire with the mitral annulus central axis (120) than can be obtained from the standard delivery devices that cross the fossa ovalis (40) from below via the inferior vena cava (IVC) (130). When crossing the atrial septum (50) from below (via the IVC (130)), the physician is able to use the thickened limbus (140) of the fossa ovalis (40) to direct a standard access catheter (not shown) across the atrial septum (50); a therapeutic catheter, such as a TMVR device (which is delivered across the mitral annulus (90) via a TMVR catheter and sheath) must then undergo a large curved path of over 135 degrees in order for the TMVR axially directed axis (110) to stay collinear with the mitral annulus central axis (120). The result is that the TMVR device is forced into direct contact with an outside portion (150) of the mitral annulus (90) compromising the accurate placement and alignment of the TMVR device across the mitral annulus (90).

Figure 1B:
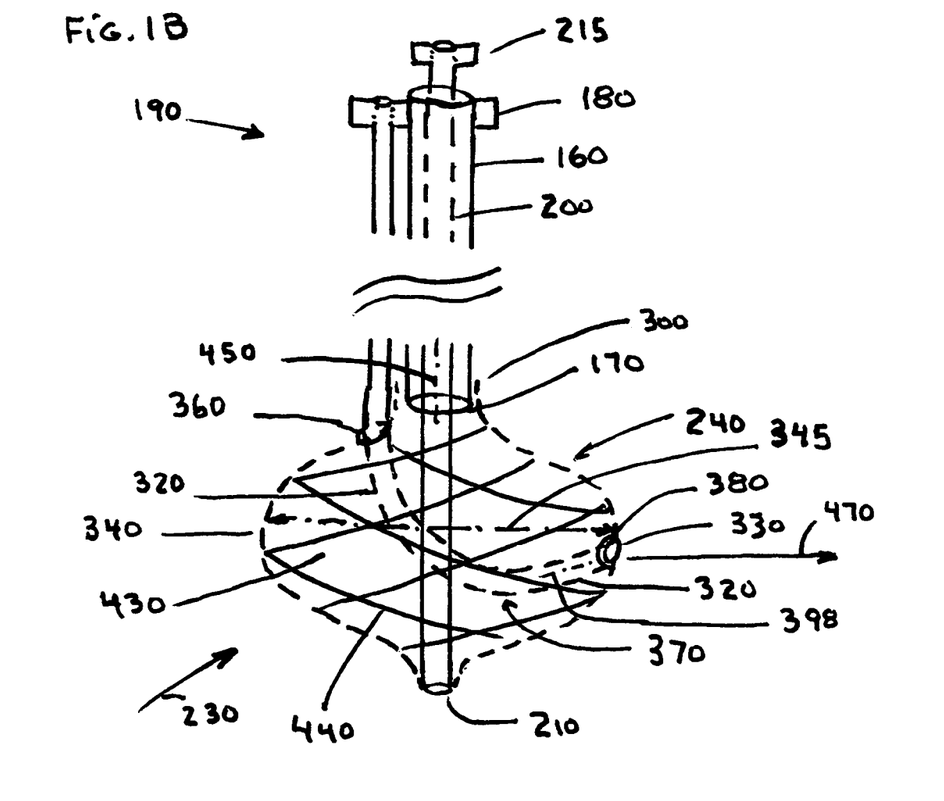
FIG. 1B is a plan view of the access catheter in an expanded larger diameter configuration showing the delivery tube located in the interior of the braided expandable structure.

One embodiment for the access catheter (10) of the present invention is shown in various stages of expanded configuration in FIGS. 1A-1F. As shown in FIG. 1A the access catheter (10) is delivered into the RA (20) from the SVC (30). The access catheter (10) has an outer shaft (160) that extends from an outer shaft distal end (170) to an outer manifold (180) located at the proximal end (190) of the access catheter (10) as shown in FIGS. 1A and 1B. Located within the outer shaft (160) is an inner shaft (200) that extends from an inner shaft distal end (210) to an inner manifold (215) located at the proximal end (190) of the catheter. The inner shaft (200) extends distally beyond the outer shaft (160) by 35 mm (range 10 to 60 mm) and is movable axially with respect to the outer shaft (160). The inner shaft (200) and outer shaft (160) are formed from polymeric materials that are used in the construction of catheter shafts including, for example, Nylon, Pebax, and others. The inner shaft (200) and outer shaft (160) can be formed such that a braided construction is contained within the walls of the shafts such that the access catheter (10) is able to be rotated at the proximal end (190) of the catheter and obtain torque transmittal and rotation at the distal end of the catheter. The inner shaft (200) provides for passage of a guidewire (220) that allows over the wire delivery of the access catheter (10) through the vasculature to reach the RA; a 0.035 guidewire (220), for example, can be placed from the subclavian vein, through the SVC (30), through the RA (20), and into the IVC (130) to provide passage of the access catheter (10) into the RA (20).

An expansion member (230) can have a braided expansion structure (240), for example, that is formed from a braided tube (250) that can expand in diameter. The expansion member can have a smaller unexpanded diameter (260) that corresponds with a larger expansion member length (270); the expansion member has a larger expansion diameter (280) that corresponds with a smaller expansion member length (290). The braided expansion structure (240) has a proximal braided end (300) that is attached to the outer shaft distal end (170); the braided expansion structure (240) extends distally to a distal braided end (310) that is attached to the inner shaft distal end (210). The braided expansion structure (240) can be formed from a braided metal such as Nitinol, Elgiloy, stainless steel, polymeric fiber, or other material having an elastic character that will not deform plastically when bent to a radius of curvature of 5 mm or less. The attachment of the expandable braided structure can be made with an adhesive, thermal bonding, external crimping elements or other attachment methods. For the embodiment described in FIG. 1A, for example, the braided structure has an unexpanded diameter (260) as shown in FIG. 1A that ranges from 10-18 French; the length of the braided expansion structure (240) in the axial direction is 3.5 cm (range 1-6 cm). To achieve the unexpanded configuration as shown in FIG. 1A the inner shaft is placed into an inner shaft distal position (305) relative to the outer shaft in an axial direction. The length and diameter for the catheter shaft and expansion structure is generally proportional to the tubular member into which it is being placed; other smaller or larger tubular structures of the body may require larger or smaller dimensions for the shaft and expansion structure. The braided expansion structure is required to expand to a diameter that is at least three times the diameter of the outer shaft; the braided structure is able to expand to a diameter that is 10 times the diameter of the outer shaft.

The expansion structure can be formed such that it has an equilibrium shape that is in an unexpanded configuration that is a cylindrical tube having a diameter that is similar to the diameter of the outer shaft to which it is bonded, for example. Expansion of such an expansion structure requires that the inner shaft be pulled proximally under tension relative to the outer shaft. Delivery of this catheter through the vasculature in its smaller diameter configuration would not require any tension to be applied to the inner shaft since the equilibrium diameter for the expansion member is its unexpanded diameter (260). Alternately, the expansion structure can be formed with an equilibrium configuration that provides the expansion member with an expanded diameter (350). To deliver this catheter through the vasculature to a location within the right atrium, the inner shaft would be pushed distally relative to the outer shaft to form an unexpanded configuration. Release of the inner shaft distal push force would allow the expansion member to expand naturally to its equilibrium expanded diameter. The expansion structure can be placed into an intermediate diameter that is intermediate between the expanded configuration and the unexpanded configuration by controlling the relative axial position of the inner shaft relative to the outer shaft; the inner shaft can be placed between an inner shaft distal position (305) as shown in FIG. 1A and an inner shaft proximal position (605) as shown in FIG. 1D.

Figure 1C:
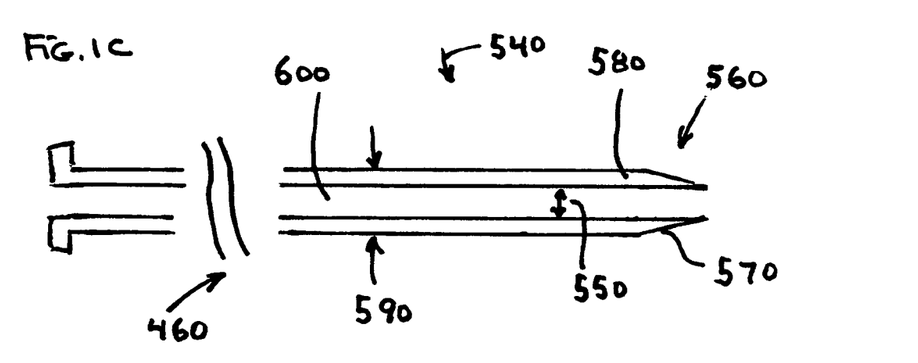
FIG. 1C is a plan view of a dilator catheter intended to be placed within the delivery tube of the access catheter.
Figure 1D:
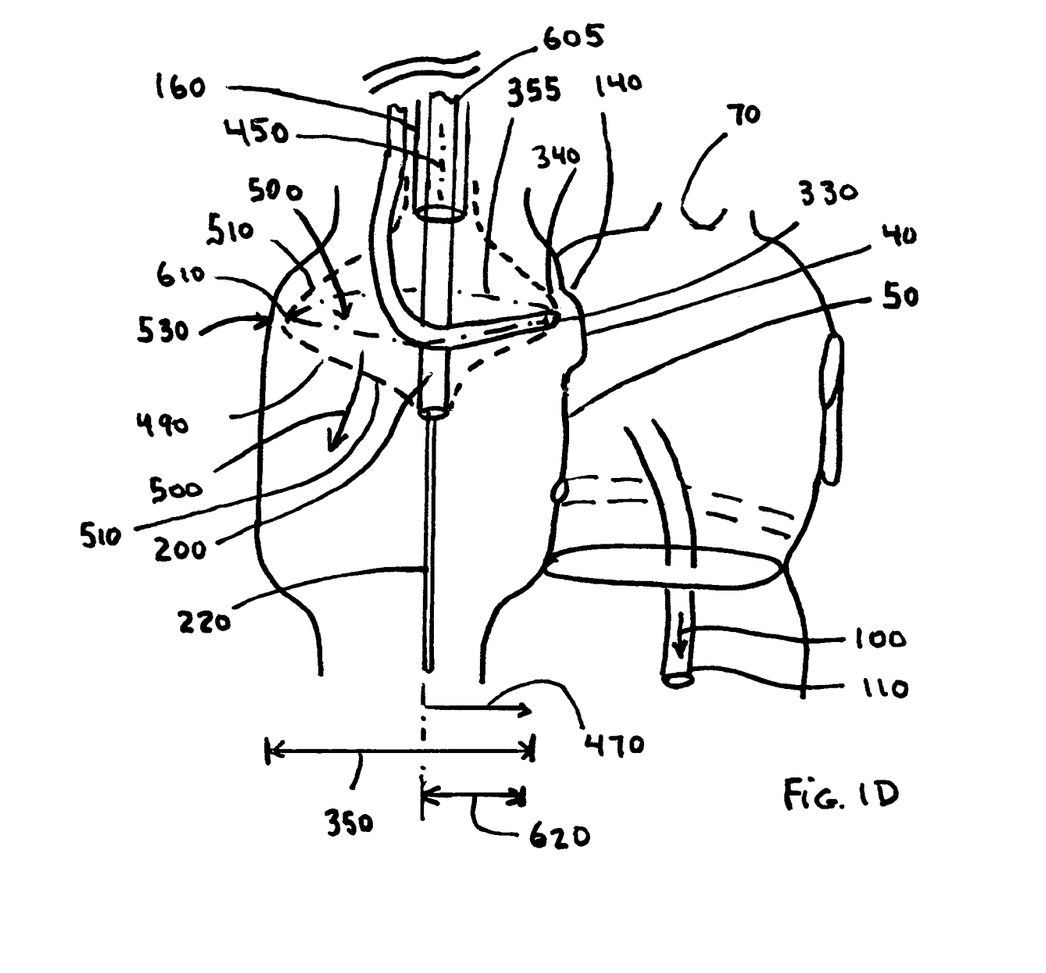
FIG. 1D is a perspective view of an expanded access catheter positioned within the right atrium and making direct contact of the delivery tube opening with the fossa ovalis and contact of the braided expansion member with the opposite wall of the right atrium.

A delivery tube (320) extends along the outer shaft (160) from the access catheter (10) proximal end (190) to a distal delivery opening (330) that is located in the central braided region (340) of the braided expansion structure (240) along a large diameter (350) as shown in FIGS. 1B and 1D. The distal delivery opening is located substantially midway between the proximal braided end (300) and the distal braided end (310) of the expansion member (230) along a perimeter of the expansion member near or on the largest diameter of the expansion member. The distal delivery opening is located in the central region of the expansion member; the central braided region is located at the braided perimeter (355) having the maximal diameter (345) of the expansion member and extends to a distance of 10% of the length of the expansion member on each side of the braided perimeter (355).

The delivery tube (320) enters a proximal braided opening (360) located near the proximal braided end (300) of the braided expansion structure. The delivery tube (320) forms a gradually curved path (370) between the braided expansion structure (240) and the inner shaft (200) from the proximal braided opening (360) to the distal braided opening (380) where the delivery tube (320) forms the distal delivery opening (330). The curved path (370) directs the delivery tube (320) through a curve of 90 degrees (range 70-120 degrees) from the axial catheter direction (450) adjacent and just proximal to the braided expansion structure to the distal delivery axis (398) of the delivery tube (320). The length of the distal portion (400) of the delivery tube (320) is sized to provide the same distal portion length (410) (integrated along a curved path of the delivery tube (320)) as is present from the proximal braided opening (360) to the distal end of the delivery tube (320) in a non-expanded configuration as shown in FIG. 1A and in an expanded configuration as shown in FIG. 1B. The delivery tube (320) therefore forms a serpentine or non-straight shape in the unexpanded configuration of the expansion member. The delivery tube (320) provides a delivery lumen (420) that is used to deliver therapeutic catheters and members used to cross the atrial septum (50); the delivery tube (320) can be attached to the outer shaft (160) or can be contained within one wall of the outer shaft (160).

The distal portion (400) of the delivery tube (320) that extends within the interior (430) of the braided expansion structure (240) from the braided opening to the distal delivery opening (330) can be formed from a polymeric material or a composite material that resists kinking; materials of construction include Pebax, Nylon, polyethylene, and other polymers used in catheter construction. The delivery tube (320) can be formed, for example, with a fiber braid contained within the wall of the delivery tube (320). The delivery tube (320) exits the braided expansion structure (240) through a second braided opening or distal braided opening (380) located in the central braided region (340) that is substantially midway along the length of the braid between the proximal braided end (300) and the distal braided end (310); the location of the distal braided opening could vary approximately 10% from the midway location between the proximal braided end (300) and the distal braided end (310). The delivery tube (320) can be bonded to the braided fibers (440) of the braided expansion structure (240) near the distal delivery opening (330) by a flexible adhesive such as polyurethane or silicone rubber, for example; other methods of attachment include sutures, thermal bonding, solvent bonding and other bonding methods. The delivery tube (320) is directed radially outward in a direction perpendicular (range 70-120 degrees) to the axial catheter direction (450) of the access catheter (10) near the braided expansion structure (240) to direct the delivery of a dilator catheter (460) or other crossing catheter contained within the lumen of the delivery tube (320) in a full radial direction (470) (range from 70-120 degrees from the catheter axial direction (450) in the distal catheter region.

Located near the distal delivery opening (330) and positioned around the delivery tube (320) is a radiopaque (RO) marker band (480). The RO marker band (480) allows the operator to position the distal delivery opening (330) to be directed toward the atrial septum (50). The catheter can be rotated to locate the RO marker to be adjacent to or directed toward the atrial septum (50). The delivery tube (320), in one embodiment intended for crossing the atrial septum (50) has an inner diameter of 0.055 inches (range 0.040-0.090 inches) and outer diameter of 0.080 inches (range 0.060 to 0.100 inches); the inner diameter of the delivery tube (320) of 0.055 inches will allow for movable passage of a dilator catheter (460) or dilator tube. The braided expandable structure is an open braided structure (490) that allows blood flow (500) to cross from the right atrium through the braided wall (510) to the interior of the braided expandable structure and flow from the interior back out into the atrium thereby not causing any impediment to blood flow (500) through the atrium with the expandable structure in an expanded configuration. Blood can flow in a distal direction (520) from the superior vena cava across the expanded braided structure and into the tricuspid valve (not shown) when the expanded braided structure is fully expanded against the atrial septum (50) and the apposed tissue (530) of the RA (20).

The distal region (540) of a dilator tube as shown in FIG. 1C can be deliverable and can travel within the entire length the delivery tube (320); the dilator tube has an inner diameter (550) of 0.035 inches (range 0.025-0.045 inches). The dilator tube fits within the delivery tube (320) and has a length that extends from the proximal end (190) of the access catheter, through the delivery lumen, and out of the distal delivery opening (330) by a distance of 5 cm (range 2-10 cm). The dilator tube is formed from a lubricious polymeric material such as polyethylene, polytetrafluoroethylene, a copolymer, or other polymeric, composite, or nonpolymeric material used for dilators, for example. The distal end (560) of the dilator tube has a bevel (570) or taper near the dilator tube distal end for a few millimeters of length such that the dilator wall (580) has a very thin dilator wall thickness (i.e., 0.005 inch, range 0.002-0.008 inch) located at the dilator distal end such that a smooth transition is formed from the crossing catheter to the outer diameter (590) of the dilator tube. The dilator tube provides a dilator lumen (600) for movable passage of a 0.035 inch outer diameter crossing catheter such as a beveled needle, a blunt needle, sharp pin, or a guidewire (220) within the dilator lumen.

Upon application of tension by the operator to the inner shaft (200) relative to the outer shaft (160) the inner shaft is placed into an inner shaft proximal position (605) relative to the outer shaft in an axial direction; the braided expansion structure (240) will expand outwards to an expanded configuration with an expansion diameter as shown in FIG. 1D. Alternately, by applying compressive or pushing movement to the outer shaft (160) relative to the inner shaft (200), the expansion structure can be placed into an expanded configuration. The central braided region (340) that is nearest the atrial septum (50) will place the distal delivery opening (330) into contact with or adjacent to the fossa ovalis (40). The opposite side (610) of the braided expansion structure (240) located 180 degrees around the expanded perimeter (355) of the braided expansion structure (240) will provide contact apposition and support against the apposed tissue of the RA (20) wall (i.e. 180 degrees around the perimeter of the RA (20) from the atrial septum (50)). The support of the apposed tissue through the braided expansion structure (240) to the distal delivery opening (330) provides support for a crossing catheter to be advanced through the delivery lumen (420) of the delivery tube (320) and across the atrial septum (50).

The expanded configuration shown in FIG. 1D provides a radial direction (470) (i.e., with at least 80% radial componency) for the delivery tube (320) near the distal delivery opening. The delivery tube (320) is altered in its direction from an axial direction (450) to a radial direction (470) that extends outwards from the catheter axis toward the distal delivery opening (330) located in the central region of the braided expandable structure (340); the radial direction (470) of the delivery tube (320) extends over a distance that is equal to the expanded braid radius (620) of the braided tubular structure. This expanded braid radius (620) is 2.0 cm (range 0.5-3.5 cm); this braided radius is much greater than the radius of the outer shaft of a catheter (i.e., one half of the outer shaft diameter (630)) used in the body; the large braided radius of the present invention allows proper direction of a crossing catheter in a radial direction (470) due to the large expansion diameter for the braided expansion structure; this radial direction (470) for the delivery tube (320) cannot be accomplished by attempting to direct a crossing catheter within a lumen that is confined by the structural diameter of a shaft of a standard delivery catheter, for example. The expanded diameter of the braided structure is at least three times the diameter of the outer shaft and is able to expand to a diameter that is more than six times the diameter of the outer shaft.

The location of the distal delivery opening (330) relative to the atrial septum (50) can be viewed under fluoroscopy or via an ultrasound catheter via the RO marker. The catheter can be positioned in an axial direction (450) within the RA (20) or via rotation within the RA (20) such that the distal delivery opening (330) is located adjacent to the limbus (140) of the fossa ovalis (40) or located elsewhere adjacent to the atrial septum (50). The inner shaft (200) can be placed into greater tension to increase the diameter of the expanded braided structure to provide support against the apposed tissue of the RA (20) located 180 degrees away from the atrial septum (50) and to place the distal delivery opening (330) into the most appropriate location adjacent to the atrial septum (50); thus the braided expansion structure (240) can be varied in its braided diameter to fit with a range of diametric sizes of the RA (20) between various patients. Generally the location of the fossa ovalis (40) nearest the limbus (140) provides the most aligned route toward the axis (120) of the mitral annulus (90) and safest route for puncturing the atrial septum (50) without negative sequellae.

Figure 1E:
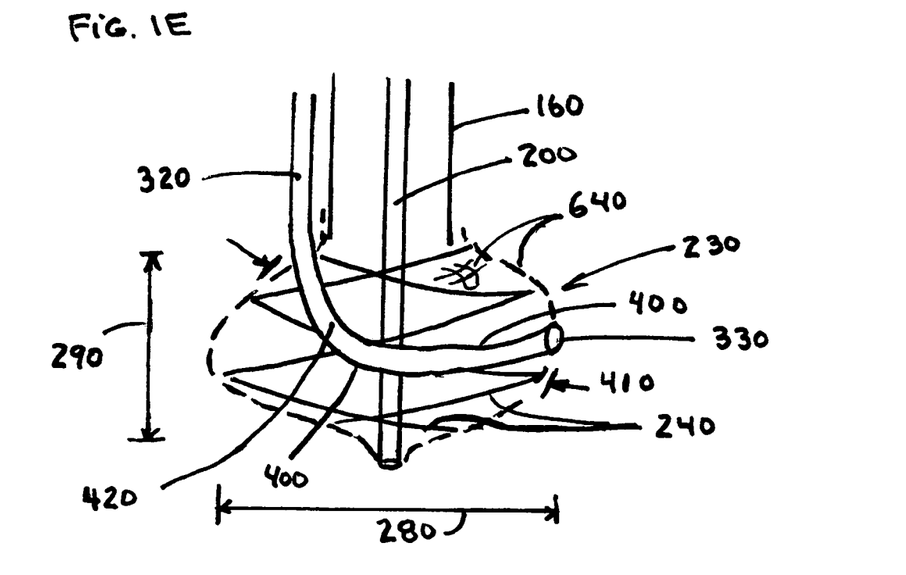
FIG. 1E is a plan view of the braided expansion member in an expanded configuration and having the delivery tube located on the outside of the braided expansion member.
Figure 1F:
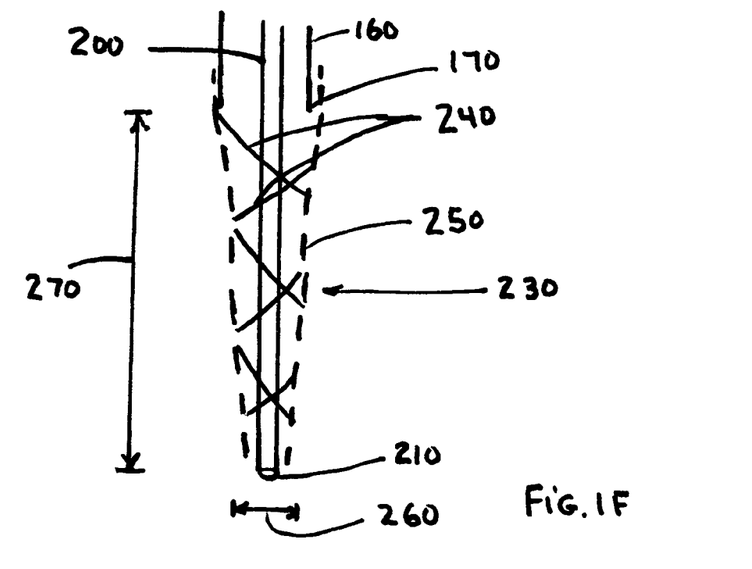
FIG. 1F is a plan view of the braided expansion member in a nonexpanded configuration.

In an alternate embodiments, the distal portion (400) of the delivery tube (320) of the access catheter (10) of the present invention can alternately be located along the outer surface (640) of the braided expandable structure as shown in FIG. 1E (rather than contained, for example, substantially within the braided expansion structure). The delivery tube (320) can be bonded to the braided fibers on the exterior surface of the braided expandable structure using adhesives including polyurethane, silicone, or other flexible adhesive for example. Other aspects of this embodiment are similar to the embodiments described in FIGS. 1A-1D.

Figure 2A:
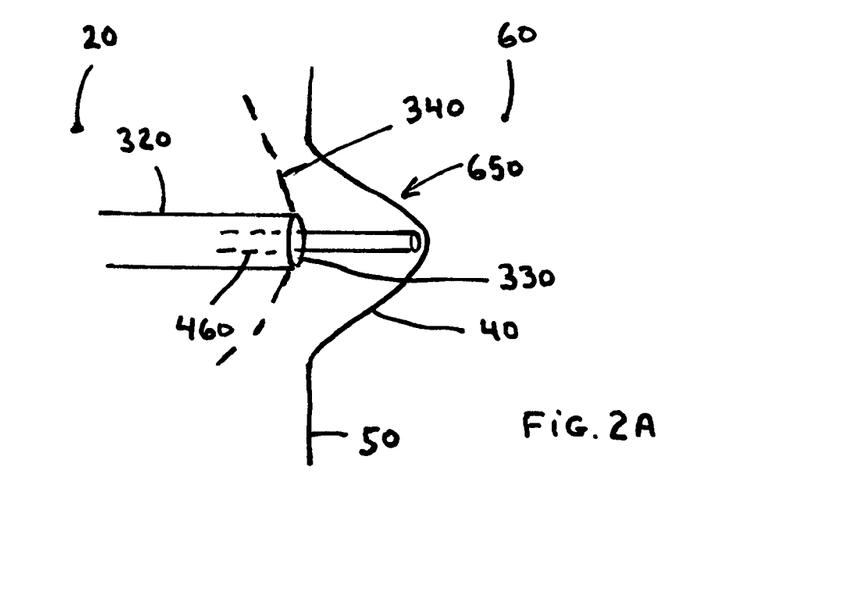
FIG. 2A is a perspective view of the central braided region of the expansion member with a dilator tube extending out of the distal delivery opening causing tenting of the fossa ovalis.

A close-up view of the central braided region (340) located adjacent to the fossa ovalis (40) is shown in FIG. 2A. A dilator tube (460) is advanced within the delivery tube (320) and into direct contact with the fossa ovalis (40) and advanced forward under compression pushing the fossa ovalis (40) outwards away from the RA (20) and toward the LA (60) (i.e., to the right as viewed in FIG. 2A) while viewing the fossa ovalis (40) via fluoroscopy or echocardiography (echo). As seen in FIG. 2A the fossa ovalis (40) is seen as forming a tented fossa ovalis (650) (i.e., referred to as tenting). The presence of tenting in the proper location is an indication that the location for the subsequent puncture of the fossa ovalis (40) is acceptable.

Figure 2B:
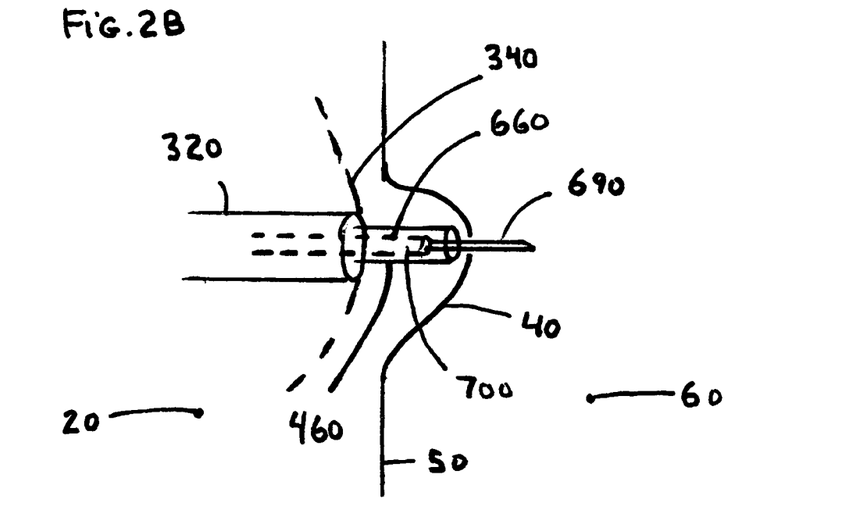
FIG. 2B is a perspective view of the central braided region of the expansion member with a sharp member extending out of the dilator tube located in the lumen of the delivery tube; the sharp member extends across the fossa ovalis.
Figure 2C:
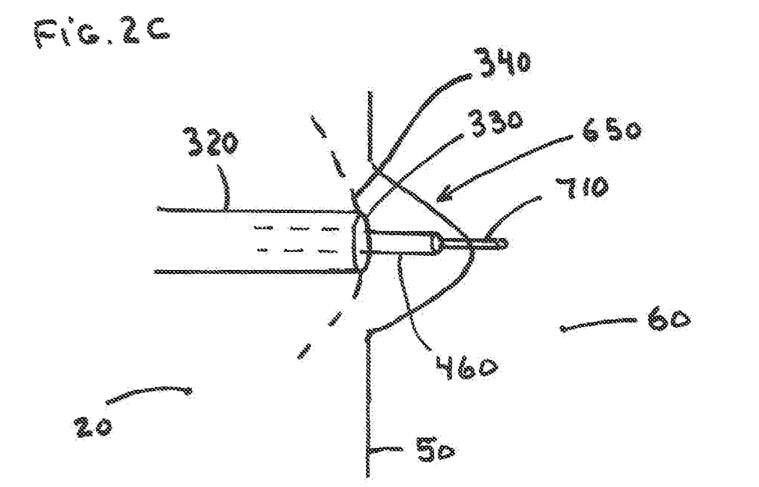
FIG. 2C is a perspective view of the central braided region of the expansion member with a beveled needle extending out of the dilator tube located in the lumen of the delivery tube; the beveled needle extends across the fossa ovalis.
Figure 2D:
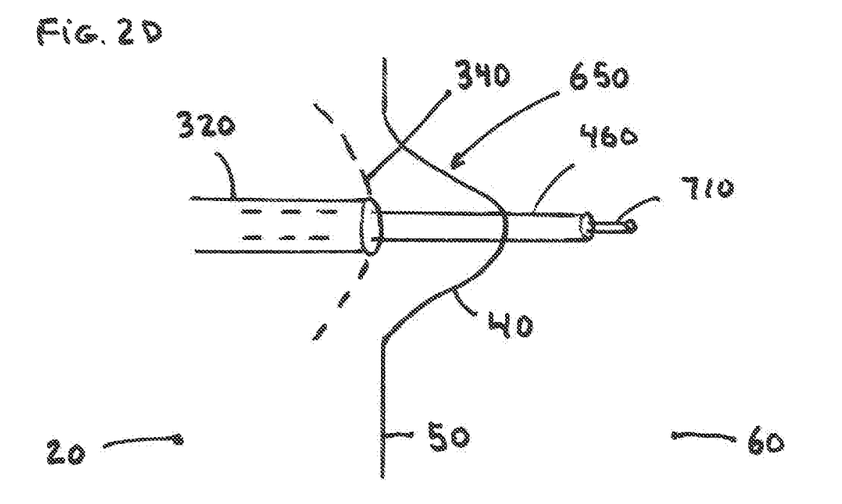
FIG. 2D is a perspective view of the central braided region of the expansion member with a beveled needle extending out of the dilator tube located in the lumen of the delivery tube; the dilator tube extends across the fossa ovalis.
Figure 2E:
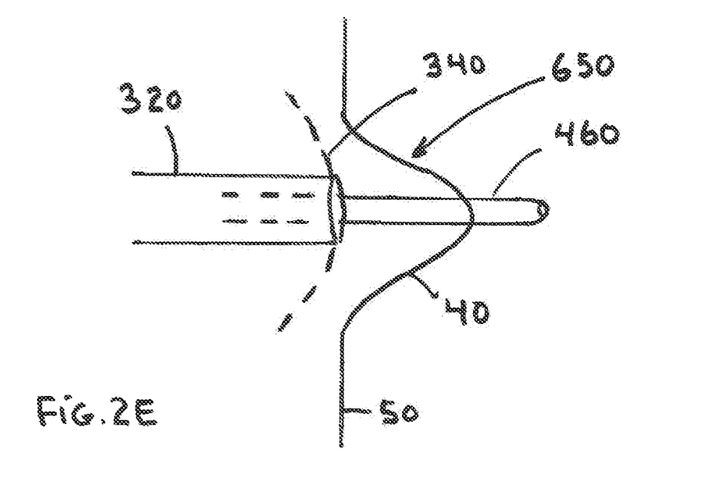
FIG. 2E is a perspective view of the central braided region of the expansion member with a dilator tube extending across the fossa ovalis.
Figure 2F:
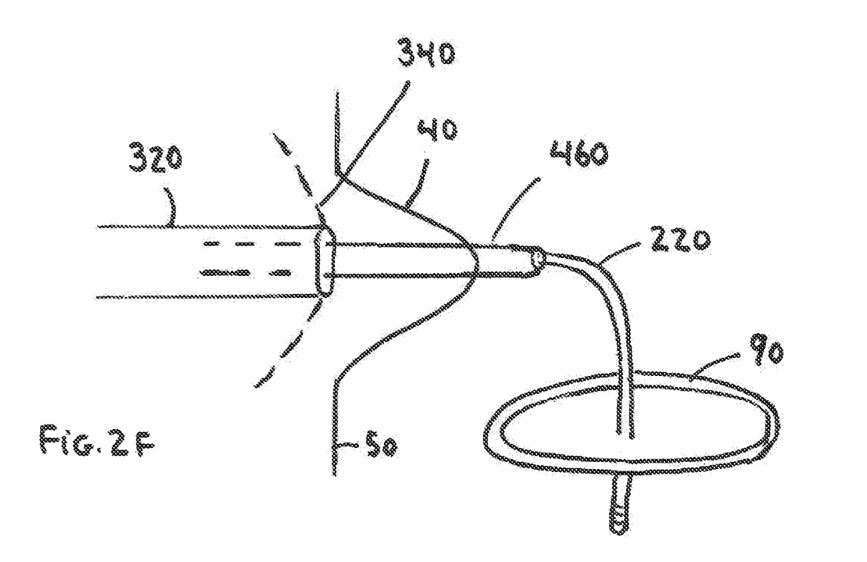
FIG. 2F is a perspective view of the central braided region of the expansion member with a dilator tube extending across the fossa ovalis and a guidewire being passed within the dilator tube and across the fossa ovalis.

As shown in FIG. 2B a crossing catheter (660) such as a blunt tipped needle (670), for example, is advanced within the dilator lumen to the fossa ovalis wall (680). A movable sharpened member (690) such as a sharpened pin, sharpened mandrel, or sharpened hollow member contained within the crossing catheter lumen (700) is advanced within the crossing catheter lumen (700) across the fossa ovalis (40) together with the crossing catheter. Once across the fossa ovalis (40) wall of the atrial septum (50), the sharpened member can be removed from the crossing catheter and a pressure measurement can be made to assess proper entry of the crossing catheter from the RA (20) to the LA (60). Alternately, as shown in FIG. 2C a beveled needle (710) can be advanced within the dilator tube (460) across the atrial septum (50) and immediate feedback to the operator regarding entry into the LA (60) is observed via a pressure change measured by the needle or via a blood visual examination. The dilator tube can then be advance over the needle and across the atrial septum (50) as shown in FIG. 2D. The needle can be removed from the dilator tube (460) while leaving the dilator tube across the atrial septum (50) as shown in FIG. 2E. A guidewire (220) that is intended for directing a TAVR device or other therapeutic catheter is then placed through the dilator tube, into the LA (60), and across the mitral annulus (90) as shown in FIG. 2F.

Figure 3A:
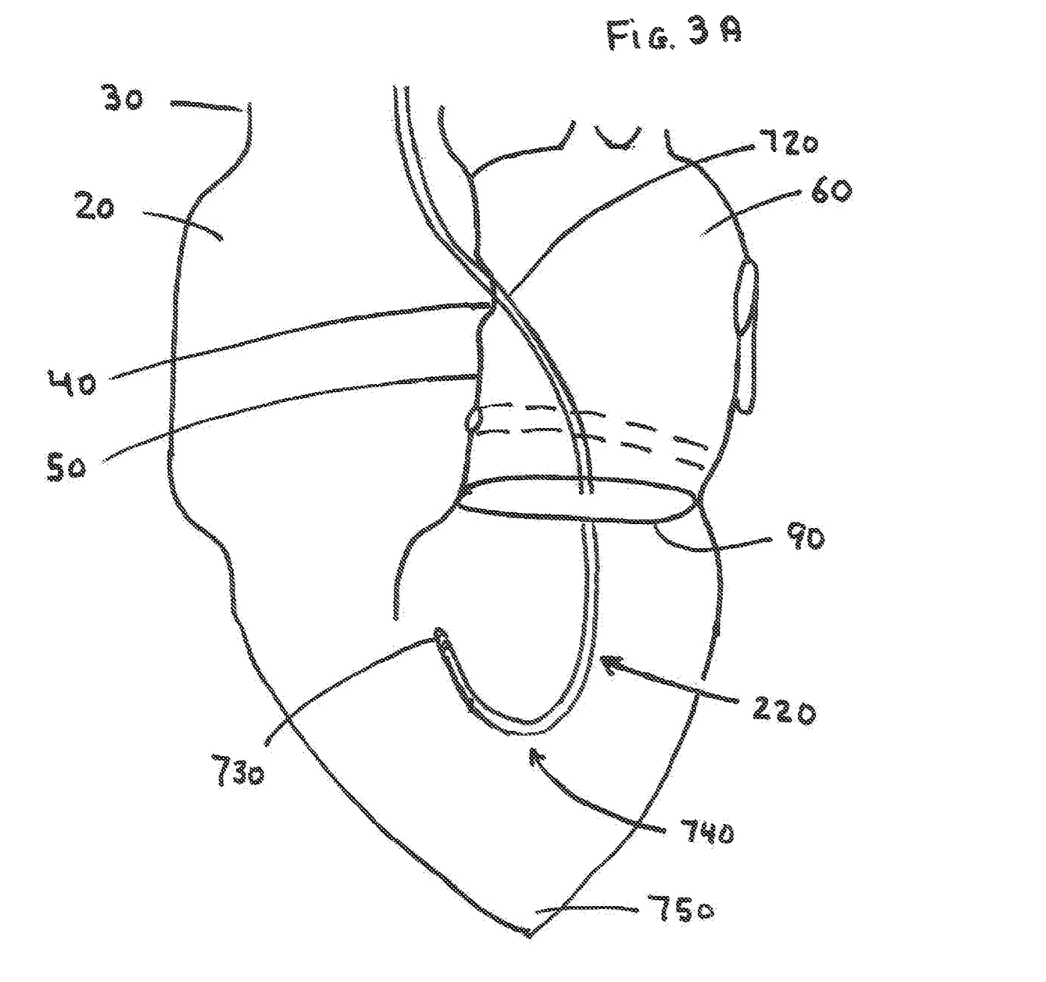
FIG. 3A is a perspective view of a guidewire that has been placed from the superior vena cava across the fossa ovalis and across the mitral annulus using the access catheter.

With the guidewire (220) in place the access catheter (10) and dilator tube are removed from their location within the RA (20) of the heart as shown in FIG. 3A. The guidewire (220) (0.035 inch diameter) should have a stiff shaft (720) extending through the fossa ovalis (40) of the atrial septum (50) and through the mitral annulus (90). The stiffness of the guidewire (220) should gradually and continuously be reduced from a location near the fossa ovalis (40) to the guidewire end (730) located in the LV. The curvature (740) of the guidewire (220) should be curved to match the shape of the apex (750) of the LV and continue to curve toward the left ventricular outflow tract or base of the heart (760) forming a gentle loop. The portion of the loop located in the apex should be of moderate stiffness and curved to match the curve of the LV apex to ensure that the apex is not perforated by the guidewire (220).

Figure 3B:
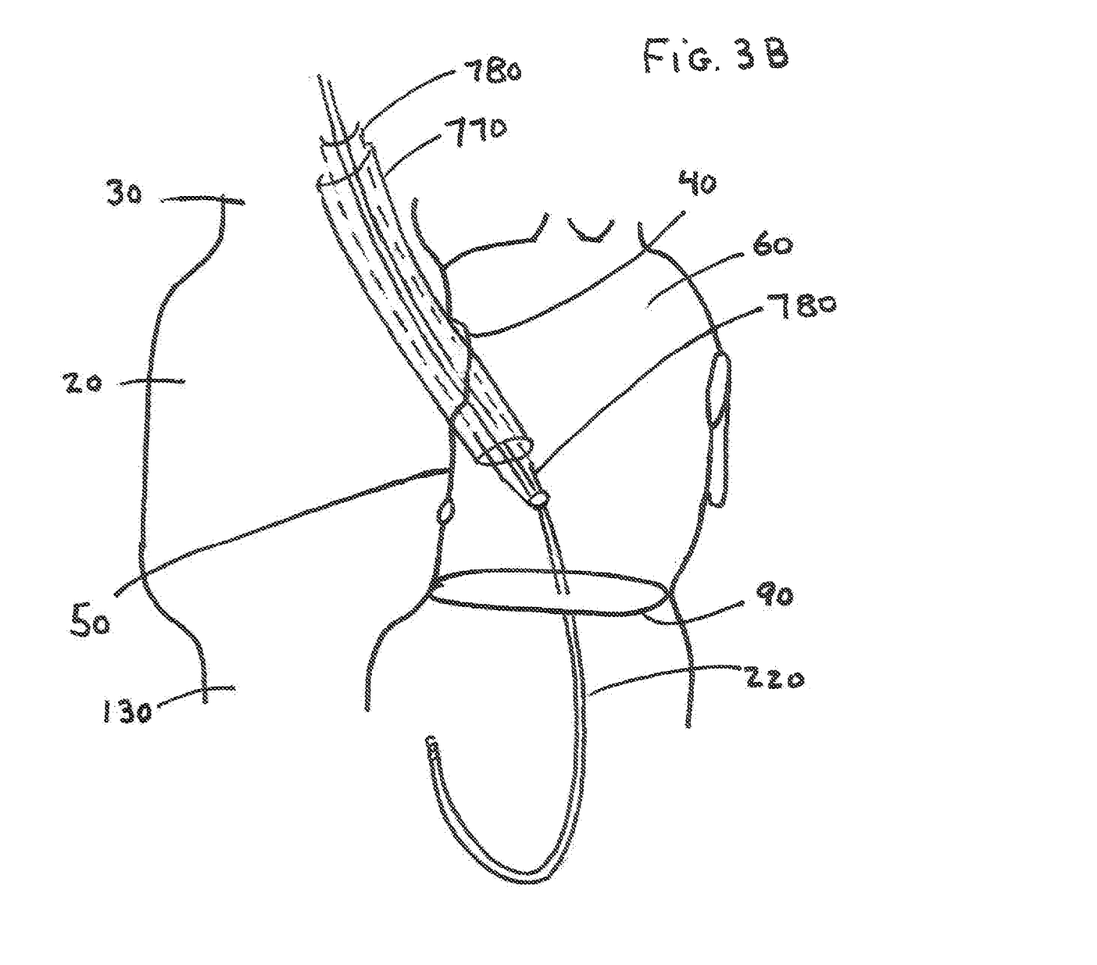
FIG. 3B is a perspective view of an introducer sheath placed across the fossa ovalis and a therapeutic catheter being delivered within the introducer sheath and over a guidewire that has been placed across the fossa ovalis.

A standard large bore delivery sheath (770) (i.e., 20-30 French, for example) and large bore dilator (780) are advanced over the guidewire (220) and into the LA (60) as shown in FIG. 3B. The large bore dilator is then removed leaving the large bore sheath positioned across the atrial septum (50) ready for passage of a TMVR device within the lumen of the large bore delivery sheath (770). The access catheter (10) of the present invention is intended to be placed into the RA (20) from the SVC (30); the present invention also provides for delivery of the access catheter (10) via the IVC (130) in a manner that is similar to that described in the present patent application but with access to the RA (20) from the IVC. Also the present invention can be used to provide access to any vessel or tubular member of the body that extends off of an atrium or chamber that is larger than the tubular member that is intended for access; the present invention is well suited to direct a catheter into a tubular member that is extending with radial componency from the main direction of the access catheter (10) as it enters into the chamber of the body.

Figure 4A:
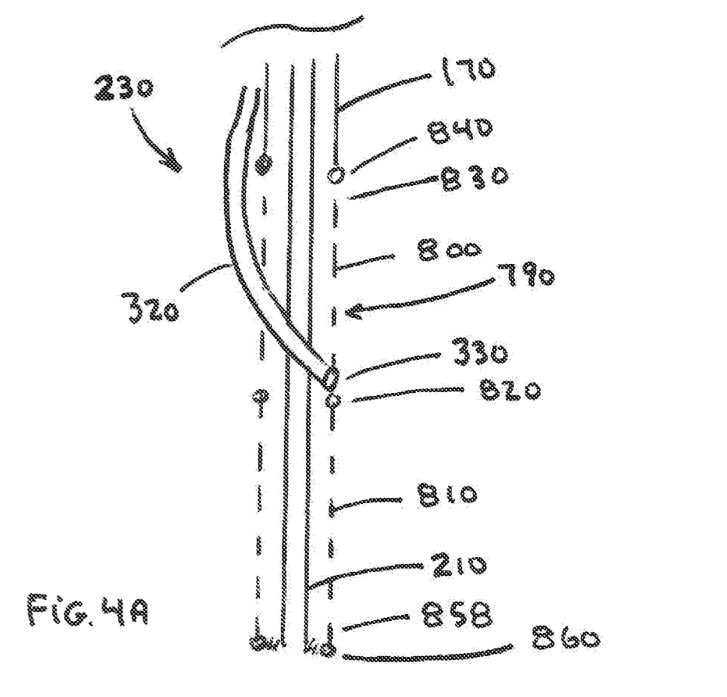
FIG. 4A is an embodiment for the expandable member of the access catheter having legs that are connected by hinges; the expandable member is in a nonexpanded configuration.
Figure 4B:
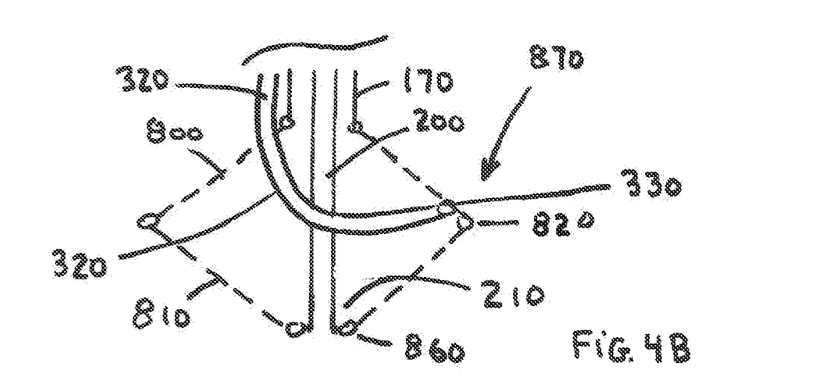
FIG. 4B is an embodiment for the expandable member of the access catheter having legs that are connected by hinges; the expandable member is in an expanded configuration.

Alternate embodiments for the expandable structure (230) are anticipated. In one embodiment the expandable structure is an expandable hinged structure (790) formed from upper legs (800) and a lower legs (810) that are joined together by middle hinges (820) as shown in FIGS. 4A and 4B. The proximal ends (830) of the upper legs (800) are joined to the outer shaft distal end (170) via upper hinges (840); the distal ends (850) of the lower legs (810) are joined to the inner shaft distal end (210) via lower hinges (860). The upper legs (800) and lower legs (810) are formed from linkages that are metal or polymeric rods or bars that extend between the upper hinges and the middle hinges, and between the middle hinges and the lower hinges. In the non-expanded configuration as shown in FIG. 4A the upper legs (800) and lower legs (810) lie adjacent to the inner shaft (200) as the inner shaft (200) his held in compression. To expand the expandable hinge structure outwards as shown in FIG. 4B, the inner shaft (200) is pulled under tension. The middle hinges move outwards; the distal portion (400) of the delivery tube (320) is attached to the middle hinge on one side (870) of the expandable hinge structure; the distal delivery opening (330) is directed outward in a radial direction (470) as described in the earlier embodiments of FIGS. 1A-1E.

Figure 5A:
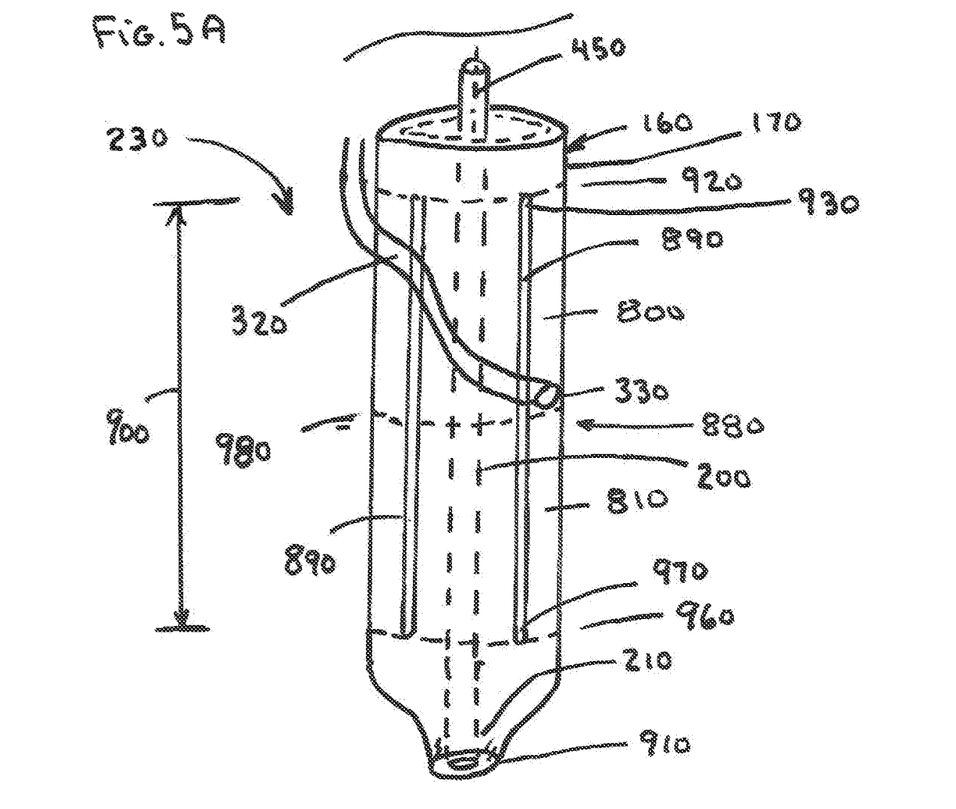
FIG. 5A is an embodiment for the expandable member of the access catheter having legs that are connected by hinge regions; the expandable member is in a nonexpanded configuration.
Figure 5B:
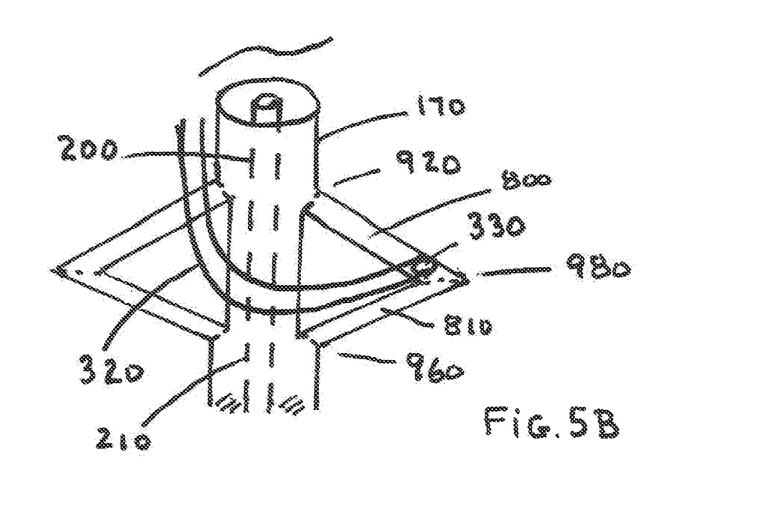
FIG. 5B is an embodiment for the expandable member of the access catheter having legs that are connected by hinge regions; the expandable member is in an expanded configuration.

An additional embodiment for the expandable structure is a hinge region structure (880) shown in FIGS. 5A and 5B. In this embodiment the distal portion of the outer shaft (160) has 6 slits (890) (range 3-9 slits) spaced along the perimeter of the outer shaft and formed by cutting through the entire outer shaft (160) wall thickness; the slits extend in an axial direction (450) to form the expandable hinge structure as shown in FIG. 5A. The slits have a slit length (900) of 3 cm (range 1-5 cm) in the axial direction; between each of the axial slits are upper legs (800) and lower legs (810) that extend axially along the length of the slits. The distal end (910) of the expandable structure is bonded to the inner shaft distal end (210). An upper hinge region (920) located at the slit proximal end (930) is formed in each of the legs; the hinge region is a weakened region of a leg that preferentially bends rather than other regions of the leg. A hinge region is formed by scoring the leg part-way through the leg wall thickness (950); such scoring can be performed via a laser or via mechanical cutting, for example. A lower hinge region (960) is formed at the slit distal end (970); a middle hinge region (980) is formed at a central region (990) located axially between the upper hinge region and lower hinge region. The proximal end of the expandable hinge region structure is formed to be contiguous with the outer shaft distal end (170) or is attached to the outer shaft distal end (170).

Upon application of tension to the inner shaft (200) the expandable hinge region structure will become larger in diameter as shown in FIG. 5B. The delivery tube (320) is bonded to one of the legs near or at the middle hinge region; bonding can be attained by adhesives, thermal bonding, solvent bonding, physical attachment, or other methods of bonding. The distal delivery opening (330) is directed outwards in a radial direction (470) as described in earlier embodiments. Other aspects of this embodiment are similar to the embodiments described in FIGS. 4A and 4B.

The invention claimed is:

1. An access catheter for crossing the wall of a tubular member of the body comprising;
   A. an elongated outer shaft having an outer shaft distal end, said outer shaft extending to a proximal region of said access catheter,
   B. an elongated inner shaft that extends within a lumen of said outer shaft, said inner shaft extending distally beyond said outer shaft distal end to an inner shaft distal end, said inner shaft extending proximally to said proximal region of said access catheter,
   C. an expandable open mesh structure positioned along a distal region of said access catheter, said expandable open mesh structure being attached to said outer shaft distal end at a first end of said expandable open mesh structure, and attached to said inner shaft distal end at a second end of said expandable open mesh structure,
   D. said expandable open mesh structure having an unexpanded configuration with a first diameter located midway between said first end and said second end of said expandable open mesh structure with said inner shaft positioned in a distal position relative to said outer shaft, said expandable open mesh structure having an expanded configuration with a second diameter larger than said first diameter, said second diameter being least three times larger than a diameter of said outer shaft, said second diameter having said inner shaft in a position with respect to said outer shaft that is more proximal than said distal position,
   E. a delivery tube that extends from said proximal region of said access catheter to said distal region of said access catheter, said delivery tube having a distal end that is bonded to said expandable open mesh structure to form an attachment along a perimeter of said expandable open mesh structure substantially midway between said first end and said second end of said expandable open mesh structure, wherein said distal end of said delivery tube is configured to form said attachment to said expandable open mesh structure in said expanded configuration and said nonexpanded configuration,
   F. said delivery tube having a delivery tube lumen that extends from said proximal region of said access catheter to said distal end of said delivery tube, said distal end of said delivery tube having a distal delivery opening that is directed radially outward away from a central axis of said access catheter with said expanded structure in said expanded configuration, wherein said delivery tube is configured to carry a dilator tube through said delivery tube lumen and extend out of said distal end of said delivery tube and into the tubular member of the body.

2. The access catheter of claim 1 further comprising said dilator tube, said dilator tube configured to extend within said lumen of said delivery tube, said dilator tube having a beveled distal end, said dilator tube extending out of said distal delivery opening in a radial direction.

3. The access catheter of claim 2 wherein said dilator tube provides passage for a crossing catheter, said dilator tube directing said crossing catheter in a radial direction, said crossing catheter comprising a needle or a guidewire.

4. The access catheter of claim 1 wherein said expandable open mesh structure has an open surface that allows blood flow to pass freely through an outer surface of said expandable open mesh structure from said first end of said expandable open mesh structure to said second end of said expandable open mesh structure while said expandable open mesh structure is configured to make contact along a perimeter of said expandable open mesh structure with a perimeter of the tubular member.

5. The access catheter of claim 1 wherein said expandable open mesh structure is a braided expandable open mesh structure comprised of a braided tube.

6. The access catheter of claim 1 wherein a portion of said delivery tube extends in an interior region of said expandable open mesh structure.

7. The access catheter of claim 1 wherein a portion of said delivery tube extends along an outer surface of said expandable open mesh structure.

8. The access catheter of claim 1 wherein said expandable open mesh structure has said expanded configuration as an equilibrium configuration for said expandable open mesh structure.

9. The access catheter of claim 1 wherein said expandable open mesh structure has said unexpanded configuration as an equilibrium configuration for said expandable open mesh structure.

10. An access catheter for crossing the wall of a tubular member of the body comprising;
    A. an elongated outer shaft having an outer shaft distal end, said outer shaft extending to a proximal region of said access catheter,
    B. an elongated inner shaft that extends within a lumen of said outer shaft, said inner shaft extending distally beyond said outer shaft distal end to an inner shaft distal end, said inner shaft extending from said inner distal shaft distal end to said proximal region of said access catheter,
    C. an expandable open mesh structure positioned along a distal region of said access catheter, said expandable open mesh structure being attached to said outer shaft distal end at a first end of said expandable open mesh structure, and said expandable member being attached to said inner shaft distal end at a second end of said expandable open mesh structure,
    D. said expandable open mesh structure having an expanded configuration with an expanded large diameter that is larger than a diameter of said outer shaft, said expanded large diameter being generated from movement of said inner shaft in a proximal direction with respect to said outer shaft, E. a delivery tube that extends from said proximal region of said access catheter to a distal end of said delivery tube, said distal end of said delivery tube being bonded to a said expandable open mesh structure to form an attachment located substantially midway between said first end and said second end of said expandable open mesh structure, said delivery tube having a distal delivery opening that is directed radially outward away from a central axis of said access catheter with said expandable open mesh structure in said expanded configuration, wherein said delivery tube is configured to carry a catheter through a lumen of said delivery tube and extend out of said distal end of said delivery tube and into the tubular member of the body.

11. An access catheter for crossing the wall of a tubular member of the body comprising;
   A. an elongated outer shaft having an outer shaft distal end, said outer shaft extending to a proximal region of said access catheter,
   B. an elongated inner shaft that extends within a lumen of said outer shaft, said inner shaft extending distally beyond said outer shaft distal end to an inner shaft distal end, said inner shaft extending from said inner distal shaft distal end to said proximal region of said access catheter,
   C. an expandable open mesh structure positioned along a distal region of said access catheter, said expandable open mesh structure being attached to said outer shaft distal end at a first end of said expandable open mesh structure, and said expandable member being attached to said inner shaft distal end at a second end of said expandable open mesh structure,
   D. said expandable open mesh structure having an expanded configuration with an expanded diameter that is larger than an unexpanded diameter of an unexpanded configuration of said expandable open mesh structure, said expanded diameter being generated from movement of said inner shaft in a proximal direction with respect to said outer shaft,
   E. a delivery tube that extends from said proximal region of said access catheter to a distal end of said delivery tube, said distal end of said delivery tube being bonded to a said expandable open mesh structure at an attachment site located between said first end and said second end of said expandable open mesh structure, said delivery tube having a distal delivery opening that is directed radially outward away from a central axis of said access catheter in said expanded configuration wherein said distal end of said delivery tube is configured to be bonded to said expandable open mesh structure in said expanded configuration and in said unexpanded configuration wherein said delivery tube is configured to carry a catheter through a lumen of said delivery tube and extend out of said distal end of said delivery tube and into the tubular member of the body.

* * * * *